(12) United States Patent
Rekow et al.

(10) Patent No.: US 12,213,799 B2
(45) Date of Patent: Feb. 4, 2025

(54) SAMPLE COLLECTOR FOR RECEIVING A BREATH GAS SAMPLE AND GAS SAMPLE TESTING DEVICE

(71) Applicant: Dräger Safety AG & Co. KGaA, Lübeck (DE)

(72) Inventors: Jens Rekow, Lübeck (DE); Sebastian Schröter, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 252 days.

(21) Appl. No.: 17/363,611

(22) Filed: Jun. 30, 2021

(65) Prior Publication Data

US 2022/0000420 A1    Jan. 6, 2022

(30) Foreign Application Priority Data

Jul. 6, 2020    (DE) .................... 10 2020 117 784.4

(51) Int. Cl.
*A61B 5/00*        (2006.01)
*A61B 10/00*       (2006.01)

(52) U.S. Cl.
CPC ........ *A61B 5/4845* (2013.01); *A61B 10/0096* (2013.01); *A61B 2010/0087* (2013.01); *A61B 2560/04* (2013.01)

(58) Field of Classification Search
CPC .............. A61B 5/4845; A61B 10/0096; A61B 2010/0087; A61B 2560/04; A61B 2560/0425; A61B 2560/0443; A61B 2560/0462; A61B 5/082; A61B 5/097; G01N 33/4972; G01N 33/0004

USPC .......................................................... 73/23.3
See application file for complete search history.

(56) References Cited

U.S. PATENT DOCUMENTS

| 3,880,591 | A  | * | 4/1975 | Burroughs ......... G01N 33/4972 |
|           |    |   |        |                         600/529 |
| 4,852,583 | A  |   | 8/1989 | Walker |
| 5,739,412 | A  |   | 4/1998 | Stock et al. |
| 2007/0191726 | A1 | * | 8/2007 | Harnoncourt ........ A61B 5/0836 |
|           |    |   |        |                         128/920 |
| 2009/0187113 | A1 |   | 7/2009 | Friedman et al. |

(Continued)

FOREIGN PATENT DOCUMENTS

| AU | 2018101008 B4 | 9/2018 |
| AU | 2019100013 B4 | 8/2019 |

(Continued)

*Primary Examiner* — Marrit Eyassu
(74) *Attorney, Agent, or Firm* — McGlew and Tuttle, P.C.

(57) ABSTRACT

A sample collector is provided for receiving a breath gas sample and a gas sample testing device is provided with such a sample collector. The sample collector is configured for receiving from a person a breath gas sample to be investigated. The sample collector includes an inflow part (2) with an inflow opening (IO) and an outflow part (13) with an outflow opening (OO). The sample collector provides a flow duct guiding a gas sample from the inflow opening (IO) to the outflow opening (OO). The inflow part (2) is rigidly connected with the outflow part (13). The inflow part (2) and the outflow part (13) together form a housing which gastightly surrounds the flow duct. The inflow part (2) tapers in a direction towards the outflow opening (OO). The outflow part (13) tapers in a direction towards the inflow opening (IO).

18 Claims, 16 Drawing Sheets

(56) References Cited

U.S. PATENT DOCUMENTS

| | | | |
|---|---|---|---|
| 2011/0098590 A1* | 4/2011 | Garbutt | A61B 5/0059 600/532 |
| 2011/0283770 A1* | 11/2011 | Hok | A61B 5/097 73/23.3 |
| 2014/0276100 A1 | 9/2014 | Satterfield et al. | |
| 2017/0238815 A1 | 8/2017 | Luxon et al. | |
| 2019/0000351 A1* | 1/2019 | Scampoli | A61B 5/0836 |
| 2020/0173981 A1 | 6/2020 | Rekow et al. | |

FOREIGN PATENT DOCUMENTS

| | | | |
|---|---|---|---|
| AU | 2018320655 A1 | 3/2020 | |
| AU | 2020100368 A4 | 4/2020 | |
| AU | 2020100588 A4 | 6/2020 | |
| CN | 202497149 U * | 10/2012 | |
| CN | 203470198 U | 3/2014 | |
| CN | 109394218 A * | 3/2019 | A61B 5/097 |
| CN | 110945356 A | 3/2020 | |
| DE | 8225425 U1 | 7/1985 | |
| DE | 102017008008 A1 * | 2/2019 | A61B 5/082 |
| WO | 2012006250 A1 | 1/2012 | |
| WO | 2012099365 A2 | 7/2012 | |
| WO | 2014165184 A1 | 10/2014 | |
| WO | 2017193175 A1 | 11/2017 | |
| WO | 2019038131 A1 | 2/2019 | |

* cited by examiner

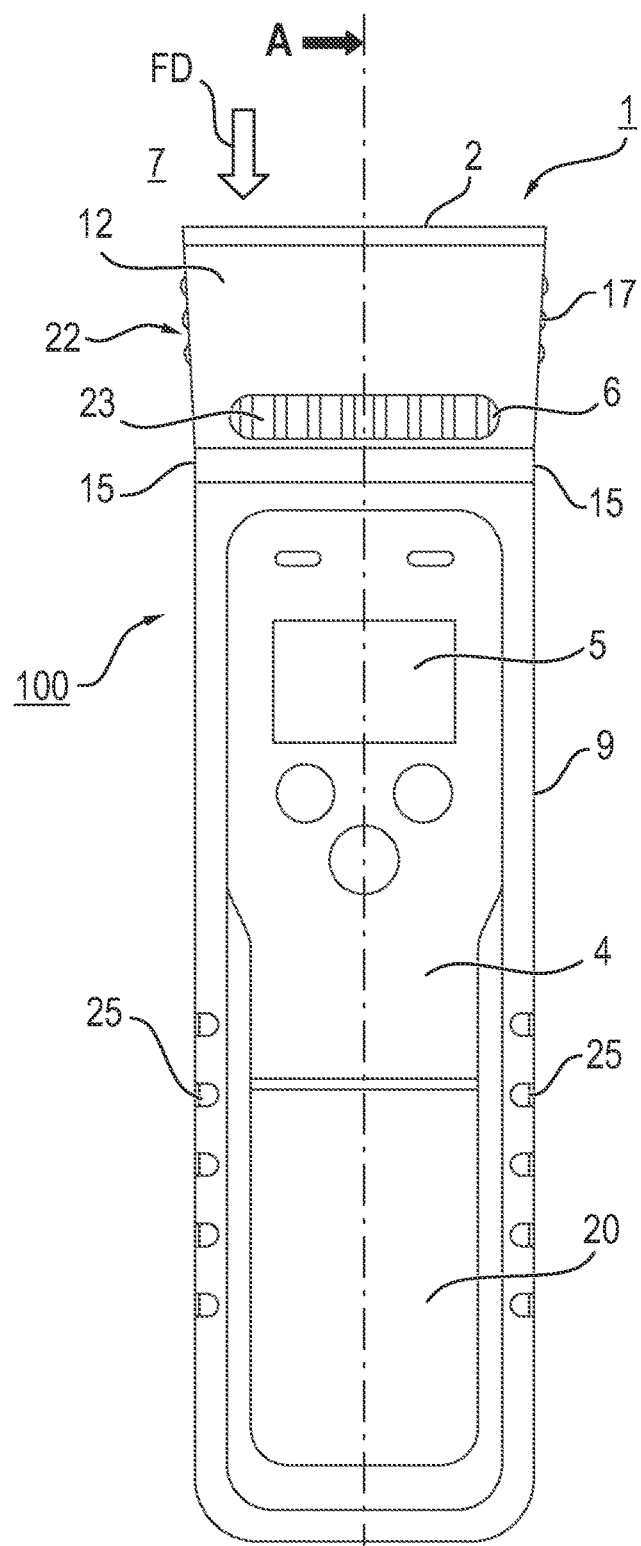
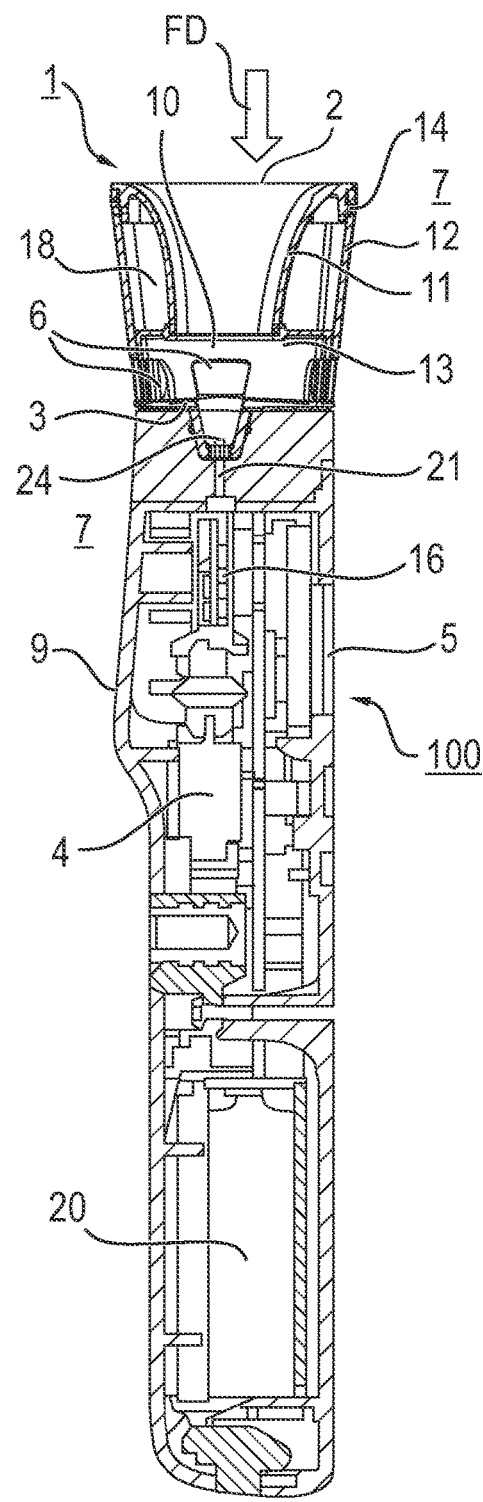
FIG. 1a
FIG. 1b

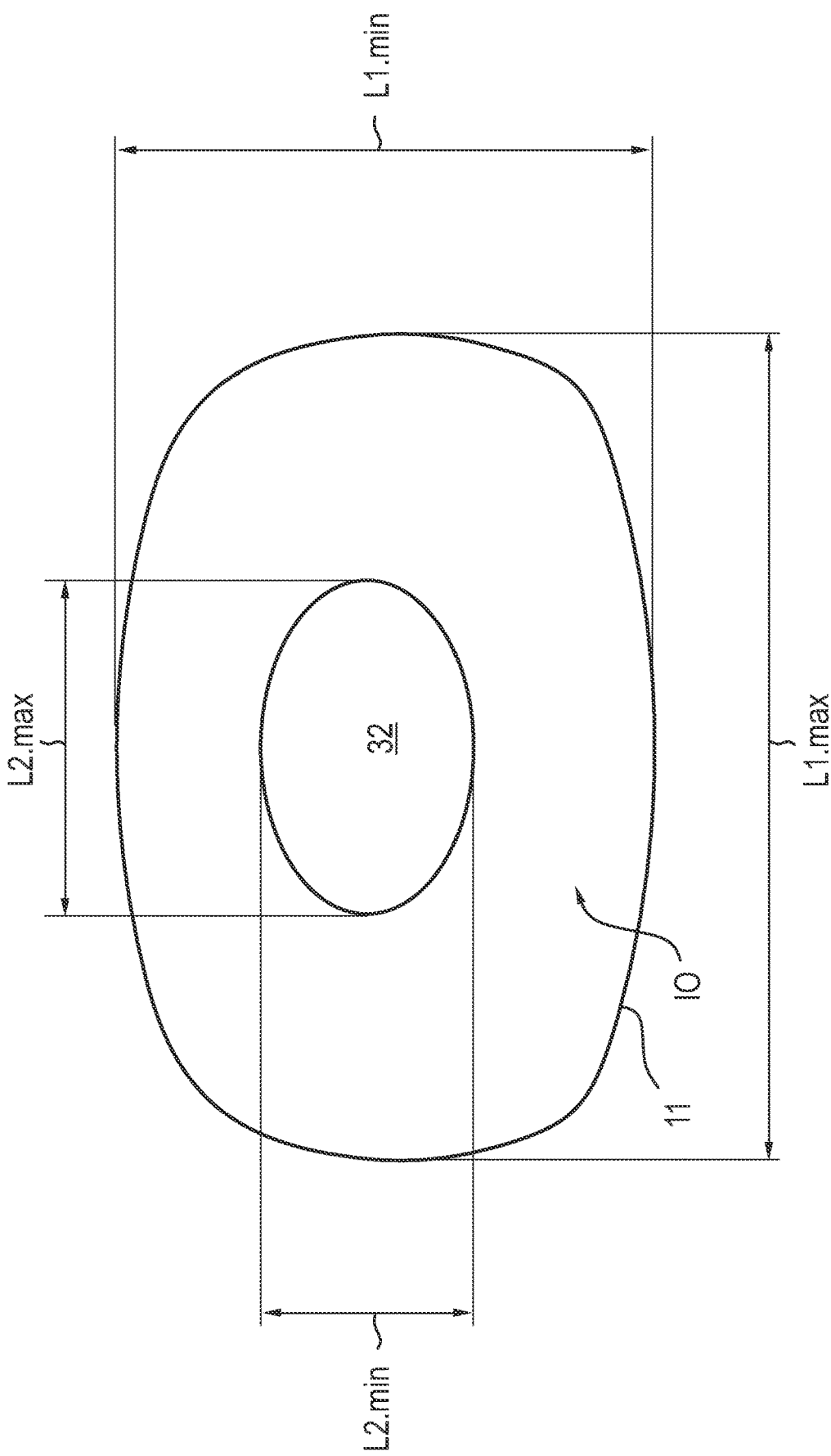

SAMPLE COLLECTOR FOR RECEIVING A BREATH GAS SAMPLE AND GAS SAMPLE TESTING DEVICE

CROSS REFERENCE TO RELATED APPLICATIONS

This application claims the benefit of priority under 35 U.S.C. § 119 of German Application 10 2020 117 784.4, filed Jul. 6, 2020, the entire contents of which are incorporated herein by reference.

TECHNICAL FIELD

The invention refers to a sample collector for receiving a breath gas sample to be investigated and a gas sample testing device with such a sample collector and a gas sensor.

TECHNICAL BACKGROUND

One application for such a sample testing device is a device wherein the sample collector receives a breath gas sample from a person. The testing device analyses the concentration of a given substance in the breath sample. In particular the device detects the presence of alcohol or a further mind-altering substance in the breath sample.

The breath gas sample flows from the person through the sample collector towards a gas sensor of the device. The gas sensor checks the received sample on the given substance.

Such breath sample testing devices are known from, e.g., AU 2018320655 A1, AU 2019100013 B4, AU 2018101008 B4, AU 2020100368 A4, and AU 2020100588 A4. DE 8225425 U1 shows a sample collector with a mouthpiece (1) and a connecting part (2) made as one piece of polypropylene.

SUMMARY

One object of the invention is to provide a gas sample collector and a gas sample testing device with such a sample collector wherein the flow of breath gas through the sample collector is improved.

This object is solved by a sample collector according to the invention and by a gas sample testing device according to the invention. Preferred embodiments are specified in this disclosure. Preferred embodiments of the sample collector are also preferred embodiments of the gas sample testing device.

The sample collector according to the invention is configured for receiving a breath gas sample, in particular a gas sample exhaled by a person towards the sample collector. The received breath gas sample is to be investigated.

The sample collector comprises an inflow part and an outflow part. The inflow part comprises an inflow opening. The outflow part comprises an outflow opening.

The sample collector provides a flow duct. This flow duct is configured for guiding a gas sample from the inflow opening through the sample collector to the outflow opening. When a person ejects a breath gas sample, the inflow opening is directed towards the person. The gas sample flows through the flow duct.

The inflow part and the outflow part together form a housing. This housing defines the flow duct and surrounds the flow duct in a gas-tight manner. Thanks to the gas-tight housing a gas sample is guided from the inflow opening to the outflow opening and can leave the flow duct only through the outflow opening (or the inflow opening) but cannot leave the housing laterally.

A gas sample flows through the flow duct from the inflow opening to the outflow opening. The gas sample flows in a flow direction through the flow duct. In the following the terms "upstream" and "downstream" refer to this flow direction.

The inflow part tapers in a direction from the inflow opening towards the outflow opening. The outflow part tapers in a direction from the outflow opening towards the inflow opening. Therefore, the cross-sectional area of the flow duct first decreases and then increases again—seen in the flow direction from the inflow opening to the outflow opening.

According to the invention the inflow part tapers in a direction towards the outflow opening. In other words: The cross-sectional area of the inflow part decreases in the flow direction. Therefore, the gas sample is concentrated in the downstream direction towards the outlet of the inflow part which is opposite to the inflow opening. This feature increases the reliability of the sample collector in combination with a gas sensor arranged downstream of the sample collector by delivering a sufficient amount of gas to the gas sensor.

According to the invention the outflow part also tapers. With other words: the cross-sectional area of the outflow part increases in the flow direction. This feature reduces the risk of a jam of gas (elevated back pressure) in the flow duct. In contrast the gas sample can expand in the outflow part.

The gas-tight housing for the flow duct provides a kind of nozzle or jet for the gas flowing from the inflow opening to the outflow opening. Thanks to this feature the flow duct better guides the gas. The risk that the flow of gas through the flow duct is perturbated is then reduced.

According to the invention the provided housing is gas-tight. Therefore, no breath gas can "escape laterally" from the flow duct. In contrast the gas which passes through the inflow opening into the flow duct can only leave this flow duct through the outflow opening (or the inflow opening).

Thanks to the gas-tight housing the risk is reduced that turbulence occurs in the flow duct. Such turbulence is caused by gas laterally or angularly "escaping" from or entering into the flow duct. In addition, the risk is excluded that air gets stuck or jams adjacent to a hole or aperture in the housing positioned between the inflow and the outflow openings. This risk is excluded because no holes are present in the housing.

Preferably the inflow part is mechanically connected with the outflow part. In one implementation the inflow part is rigidly connected with the outflow part. In a further implementation both parts are integrally formed, even monolithic, i.e. manufactured in one process step, e.g. by molding. In an alternative implementation the inflow part is separably or releasably connected with the outflow part, i.e. the two parts can be disconnected from each other.

In one embodiment the inflow opening is circular with a diameter of at least 3 cm. Preferably the shape of the inflow opening, however, differs from an ideal circle. Such a shape better fits to a gas sample testing device which can be held in one hand. The maximal dimension of the inflow opening is at least 4 cm, preferably at least 5 cm. This feature enables a contactless input of a gas sample. In particular it is possible that a person blows towards the sample collector for inputting a breath gas sample. It is not necessary that the face of the person touches the sample collector. A contactless input is more hygienic than an input by using a mouthpiece. Nevertheless, a sufficient amount of a gas sample is received by the sample collector. Preferably the dimension of the inflow opening perpendicular to the direction of the maximal dimension is at least 2.5 cm.

Preferably the maximal dimension of the outflow opening is at least 4 cm, preferably at least 5 cm. This feature ensures that enough gas can flow out of the outflow part. The risk is reduced that a jam or backflow of gas occurs while the gas sample flows through the flow duct.

Preferably the length of the inflow part, i.e. the dimension in the flow direction, is between 2 cm and 4 cm.

The inflow part and/or the outflow part may taper linearly or in a parabolic or elliptic manner, e.g.

In one embodiment the inflow part comprises an inflow part transition aperture. The inflow part tapers in a direction from the inflow opening towards the inflow part transition aperture. The outflow part comprises an outflow part transition aperture. The outflow part tapers in a direction from the outflow opening towards the outflow part transition aperture. The two transition apertures may coincide. It is also possible that one transition aperture is larger than the other one. The larger opening may encircle the smaller one.

Preferably the maximal dimension of the inflow part transition aperture is no more than 4 cm, preferably no more than 3 cm. This feature enables a sufficient amount of compression of the gas sample flowing through the inflow opening. In addition, a sufficient amount is directed towards a gas sensor downstream of the sample collector. Preferably the maximal dimension of the outflow part transition aperture is also no more than 4 cm, preferably no more than 3 cm. This feature ensures that the outflow part fits to the inflow part. Preferably the maximal dimension of the inflow part transition aperture and the maximal dimension of the outflow part transition aperture are at least 2 cm. These features reduce the risk of a jam of gas (back pressure) in the flow duct.

Preferably the respective dimension of the inflow part transition aperture is between 35% and 60% of the inflow opening in the same direction perpendicular to the flow direction. The respective dimension of the outflow part transition aperture is between 35% and 60% of the outflow opening in the same direction.

In one implementation the outflow part comprises an outflow part protrusion. This outflow part protrusion surrounds the outflow part transition aperture. A section of the inflow part engages into the outflow part transition aperture and is surrounded by the outflow part protrusion. In an alternative implementation the inflow part comprises an inflow part protrusion. This inflow part protrusion surrounds the inflow part transition aperture. A section of the outflow part engages into the inflow part transition aperture and is surrounded by the inflow part protrusion.

These implementations ensure a gas-tight housing even if the actual geometry of the inflow part and/or the outflow part differs slightly from a required geometry. Such a deviation may happen due to inevitable manufacturing tolerances. A double-wall mechanical connection between the inflow part and the outflow part is more stable than a mechanical connection just along an edge.

In one embodiment, the sample collector comprises a collector outlet which is preferably positioned downstream of the outflow part. The collector outlet comprises at least one outlet aperture, preferably several outlet apertures. The collector outlet guides a gas sample having passed the flow duct towards the or at least one outlet aperture. Preferably the collector outlet distributes the gas sample onto several outlet apertures of the collector outlet.

In another embodiment, the sample collector comprises a collector casing. This collector casing surrounds the housing formed by the inflow part and the outflow part, preferably with a distance to the housing. The flow duct is therefore positioned in the interior of the casing. The housing guides the gas sample through the interior of the casing. Preferably the collector casing comprises at least one outlet positioned downstream of the inflow part. It is also possible that the sample collector does not comprise such a collector casing such that the housing is in contact with the environment.

Due to the optional collector casing and the housing of the flow duct a dead space is provided between the casing and the housing. The inner surface of the collector casing and the outer surface of the housing form different walls of this dead space. The dead space can take the entire space between the inner surface of the collector casing and the outer surface of the housing or just a part of it. As the housing is gas-tight, no gas flowing through the flow duct can enter this dead space. It is possible that the collector casing surrounds the dead space in a gas-tight manner. It is also possible that a fluid connection between the dead space and the environment is established, e.g. through at least one opening in the collector casing.

Thanks to the collector casing and the housing, the housing can be configured in view of aerodynamic requirements of the flow duct. It is possible that a user grips and therefore touches the collector casing. The collector casing can be configured to fulfill ergonomic and hygienic requirements. It is possible that the cross-sectional area of the collector casing remains constant in a flow direction from the inflow opening to the outflow opening or tapers along the entire length therebetween. Preferably some gripping elements are mounted at the outer surface of the collector casing. Thanks to the dead space the housing and the collector casing can be configured independently from each other and to fulfill specific requirements.

In another embodiment, the inflow part can releasably be inserted into the collector casing. After being inserted, the inflow part and the connected outflow part are kept and held by the collector casing. It is possible but not necessary that the outflow part is connected with the collector casing or with the optional collector outlet.

In yet another embodiment, the collector casing is mechanically connected with the collector outlet. This makes it easier to replace the housing for the flow duct, i.e. the inflow part and the connected outflow part. Preferably this mechanical connection is gas-tight and is a rigid connection. This increases the mechanical stability.

In one implementation the outflow part comprises a separator element and a supporting element. The separator element is arranged perpendicular or angular to the flow direction and to the optional collector casing and forms one wall of the dead space. Preferably the separator element entirely bridges the distance between the housing and the collector casing. The separator element therefore reduces the risk that the collector casing is mechanically pressed together. The separator element can be flat, i.e. extend in a plane, or curvilinear, i.e. curved towards the outflow opening.

The supporting element engages the inner side of the optional collector casing and/or touches the optional collector outlet. Preferably the supporting element is in a full-area contact with the inner side of the collector casing. This feature increases the mechanical stability and guides the outflow part when the outflow part is inserted into the collector casing. Preferably the supporting element comprises at least one aperture and/or recess which coincides or at least overlaps with an aperture of the collector outlet.

A preferred gas sample testing device comprises a sample collector according to the invention. In addition, the gas sample testing device comprises a base body. The sample collector is mechanically connected with the base body. The outflow opening of the sample collector points towards the base body. The sample collector is configured to guide a received gas sample through the flow duct towards the base body. The base body comprises a gas sensor. The gas sensor is configured to detect at least one substance in a received gas sample, preferably alcohol.

As the outflow opening points towards the base body, the gas sample can flow from the inflow opening through the flow duct and the outflow opening into the base body.

In another embodiment, the sample collector is connected with the base body such that at least a part of the gas sample can flow straight ahead from the inflow opening through the flow duct and the outflow opening into the base body and to the gas sensor without being deflected. Therefore, turbulence, which may be caused by a deflection, is avoided. In an alternative embodiment the sample collector is connected with the base body such that the gas sample is deflected when flowing from the sample collector into the base body. This alternative embodiment enables a user to carry the base body in an upright position which is sometimes more ergonomic. The user can blow into the sample collector when looking in a horizontal direction.

In another embodiment, the sample collector of the gas sample testing device comprises a collector outlet with at least one first outlet aperture and at least one second outlet aperture. The collector outlet is arranged downstream of the outflow part. The collector outlet guides a gas sample, which has passed the flow duct, towards the outlet apertures and distributes the gas sample onto the first and second outlet apertures. The first outlet aperture, or every first outlet aperture, directs a gas sample to the gas sensor. The second outlet aperture, or every second outlet aperture, directs a gas sample into the environment of the gas sample testing device, thereby circumventing the base body. This embodiment reduces the risk of a flow jam (back pressure) in the sample collector. The cross-section areas and the positions of the first and second outlet apertures serve as degrees of freedom for guiding the gas sample.

The optional collector casing may comprise one further outflow opening which is arranged downstream of the outflow part. This additional opening further reduces the risk of a flow jam (back pressure).

In one application, the gas sample testing device is configured for contactlessly receiving a breath sample from a person. The person exhales breath which is partly received by the sample collector and guided to the gas sensor. Preferably the gas sample testing device can be held in one hand.

In the following the invention is described with reference to preferred embodiments and with reference to the following figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1a is a side view of the testing device;

FIG. 1b is a cross-sectional view of the testing device taken perpendicular to the view of FIG. 1a along line A-A of FIG. 1a;

FIG. 16 is a view showing the inflow opening and the inflow part transition aperture wherein the viewing direction is parallel to the flow direction.

DESCRIPTION OF PREFERRED EMBODIMENTS

Figure 2:
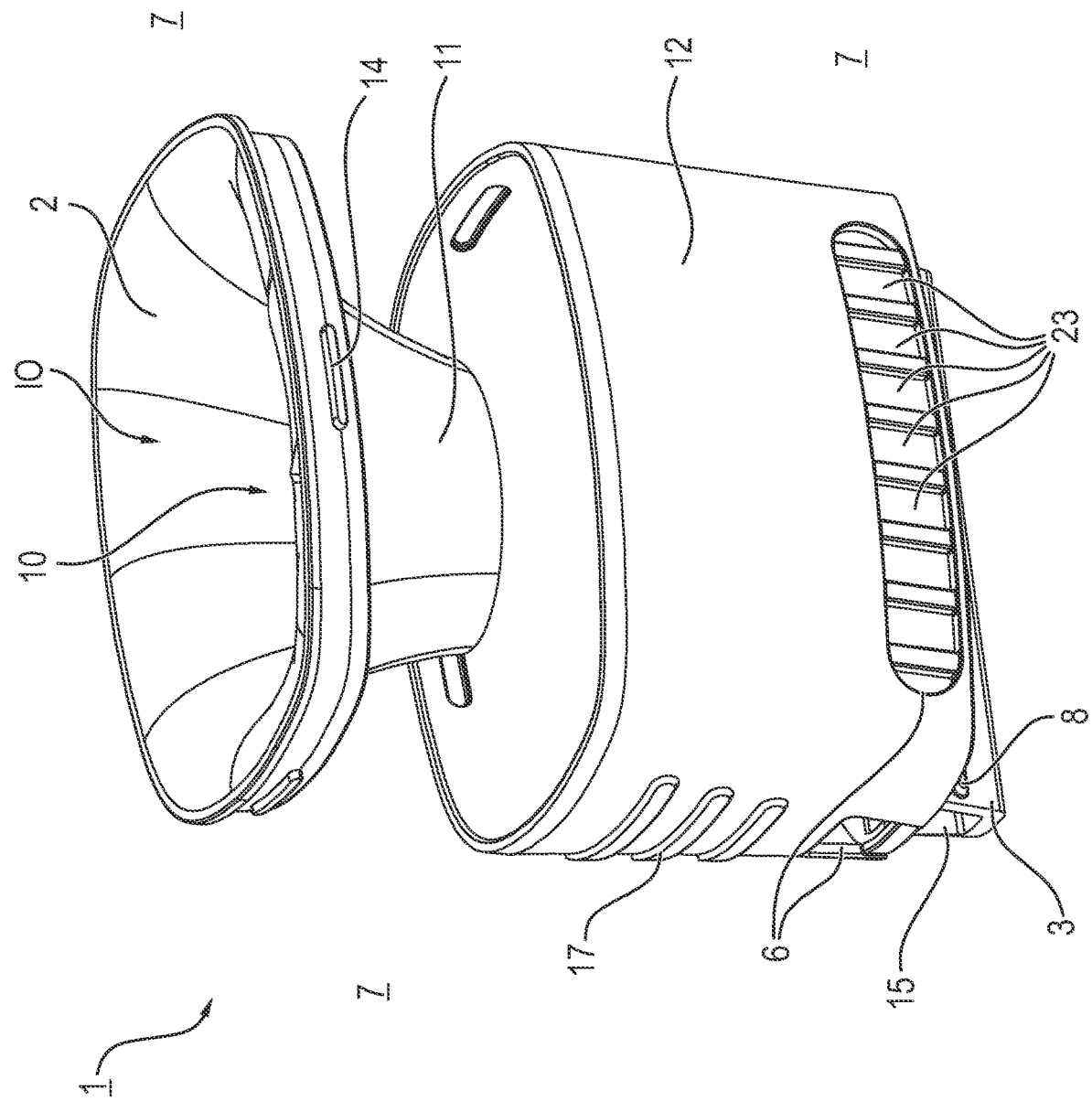
FIG. 2 is a perspective view of the collector device with the sample inlet not inserted.

Referring to the drawings, FIGS. 1a and 1b show a breath alcohol testing device 100 from two different viewing directions being perpendicular to each other. FIGS. 1a and 1b further show the area 7 surrounding the testing device 100. This testing device 100 serves as the gas sample testing device according to one embodiment of the invention.

The testing device 100 has approximately the form of a cuboid with two larger surfaces and two smaller surfaces. FIG. 1a shows the testing device 100 in a side view; FIG. 1b shows it in a cross-sectional view in the plane A-A of FIG. 1a. The testing device 100 comprises a sample collector 1 and a base body 9. The sample collector 1 can be removably connected with the base body 9. Some fastening elements 8 fasten the sample collector 1 at the base body 9, cf. FIG. 2.

A person can blow a gas sample into the sample collector 1 without touching the sample collector 1, i.e., contactlessly (in a contactless manner), and therefore with a distance between the person's face and the testing device 100. The flow direction in which the gas sample flows into the sample collector 1 is shown by an arrow FD.

The base body housing of the base body 9 surrounds a power supply unit 20 and a control unit 4. Several gripping elements 25 at the base body 9 make it easier for a person to carry the base body 9 and thereby the testing device 100. A display unit 5 in the base body housing can display measurement or test results in a human-perceptible form. A part of the injected (blown in) gas sample is guided through the gas duct 21 to an alcohol sensor 16 in the interior of the base body 9. This alcohol sensor 16 measures the alcohol concentration in the inserted gas sample. At least the measurement results of the alcohol sensor 16 enable an automatic decision whether or not the breath alcohol is above or below a given threshold. The alcohol sensor 16 can be an electro-chemical or an optical sensor, in particular an infrared sensor. Preferably the gas duct 21 guides the gas sample into a measuring chamber in the interior of the base body 9.

Figure 3:
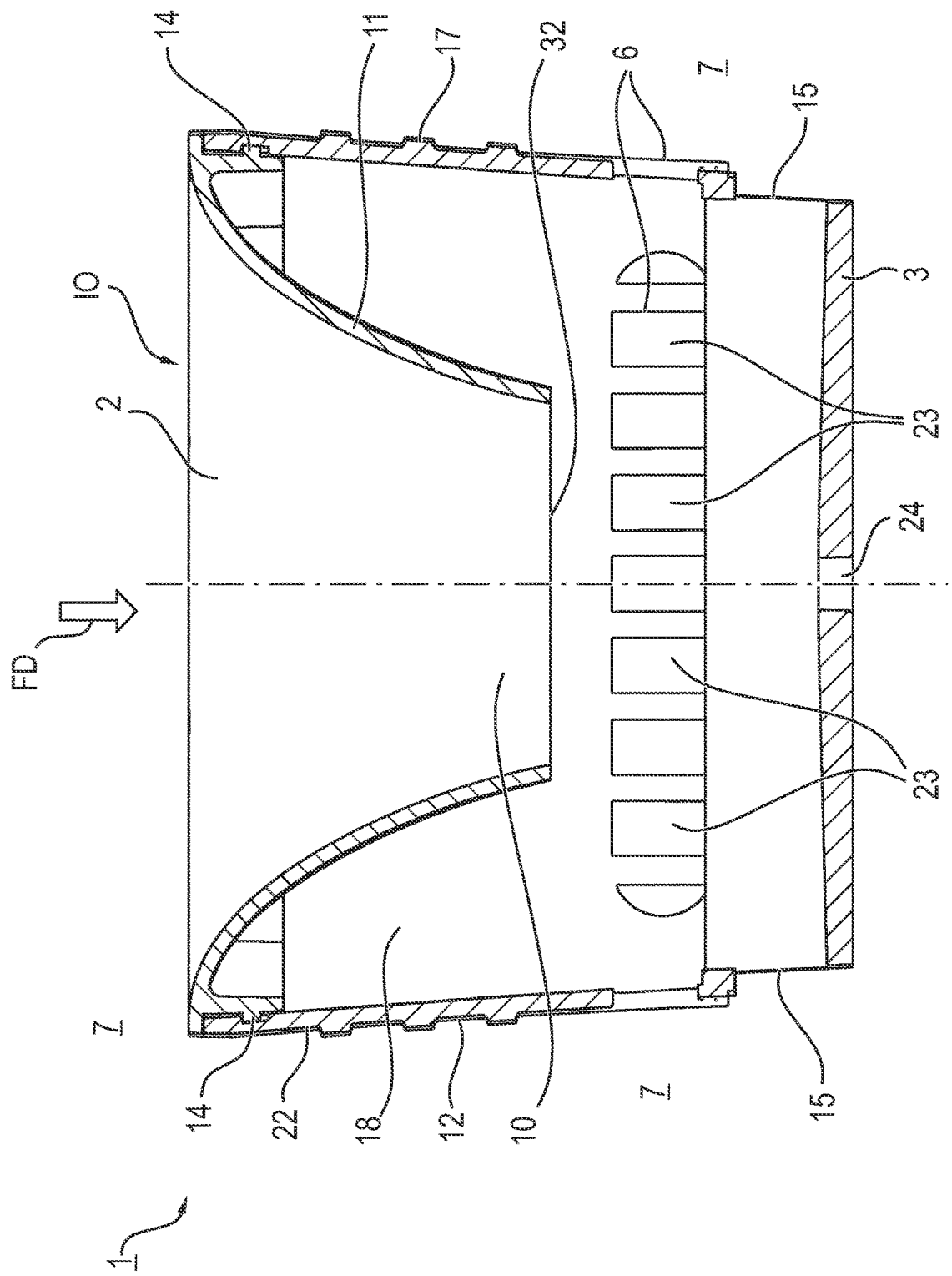
FIG. 3 is a cross-sectional view the collector device with the sample inlet inserted.
Figure 4:
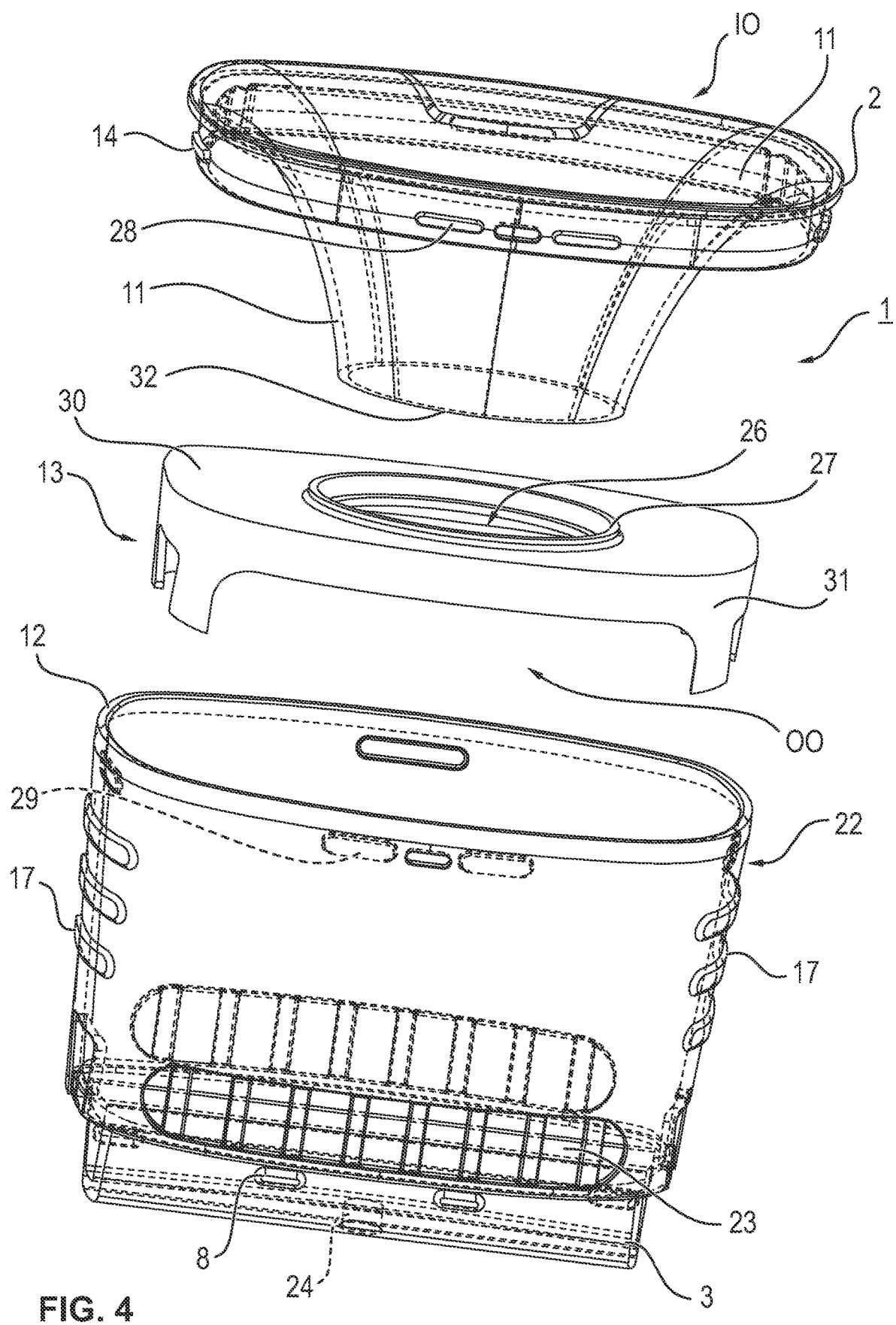
FIG. 4 is a perspective exploded view of a first embodiment of the sample collector with a flat outflow part.
Figure 5:
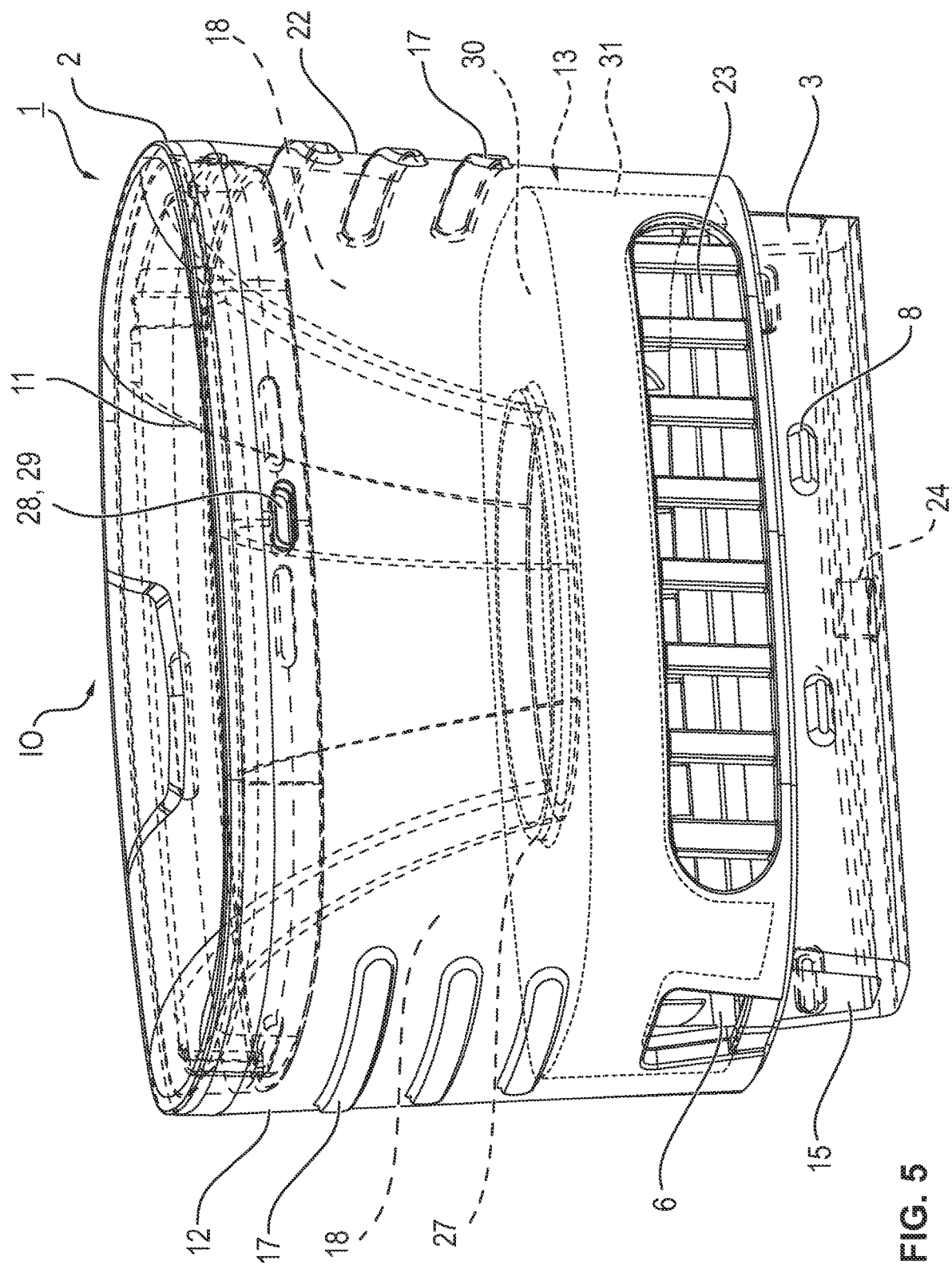
FIG. 5 is a perspective view the first embodiment with the parts assembled together.
Figure 6:
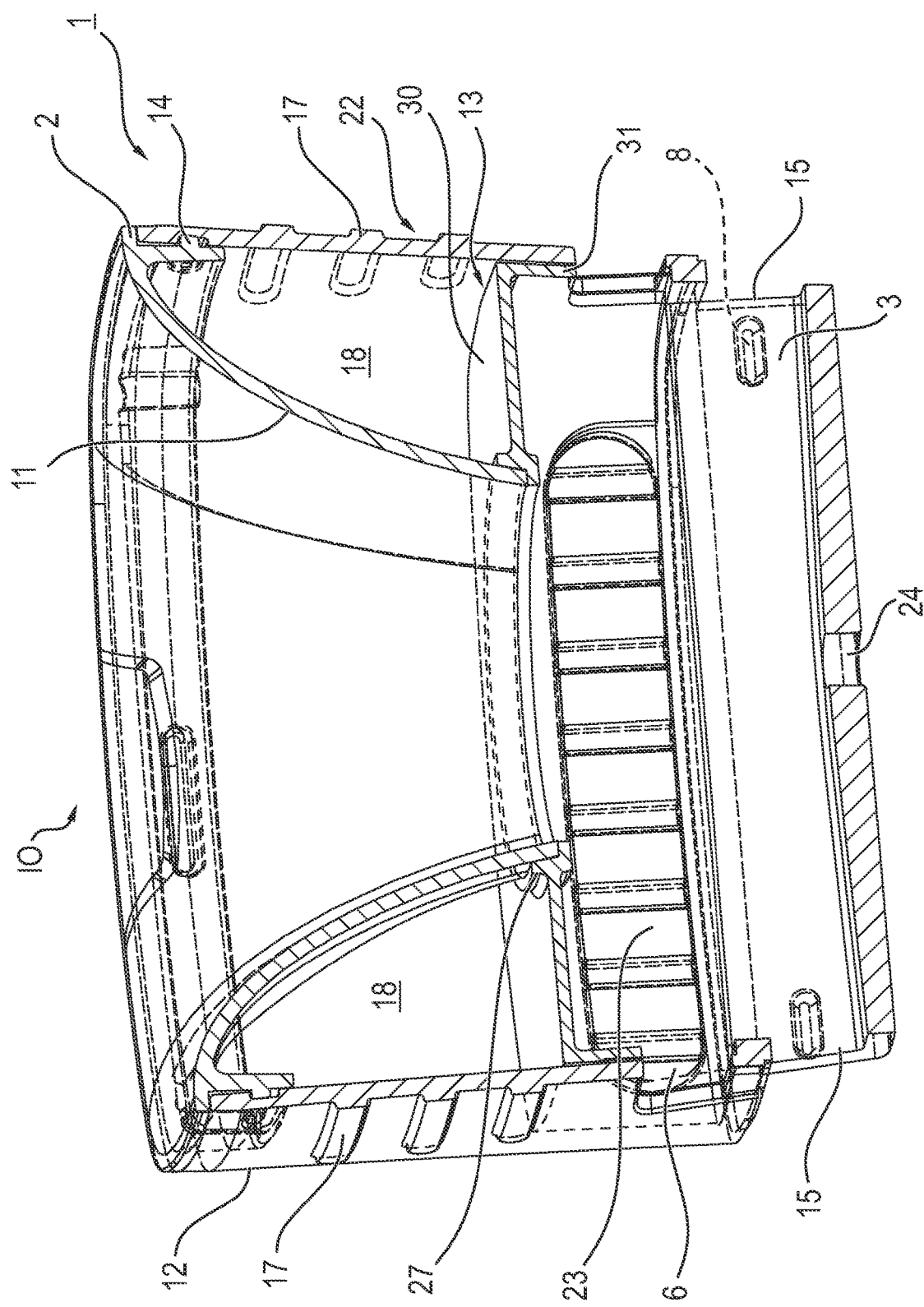
FIG. 6 is a cross-sectional view the first embodiment with the assembled parts wherein a longer axis (corresponding to a longer dimension) is in the drawing plane.
Figure 7:
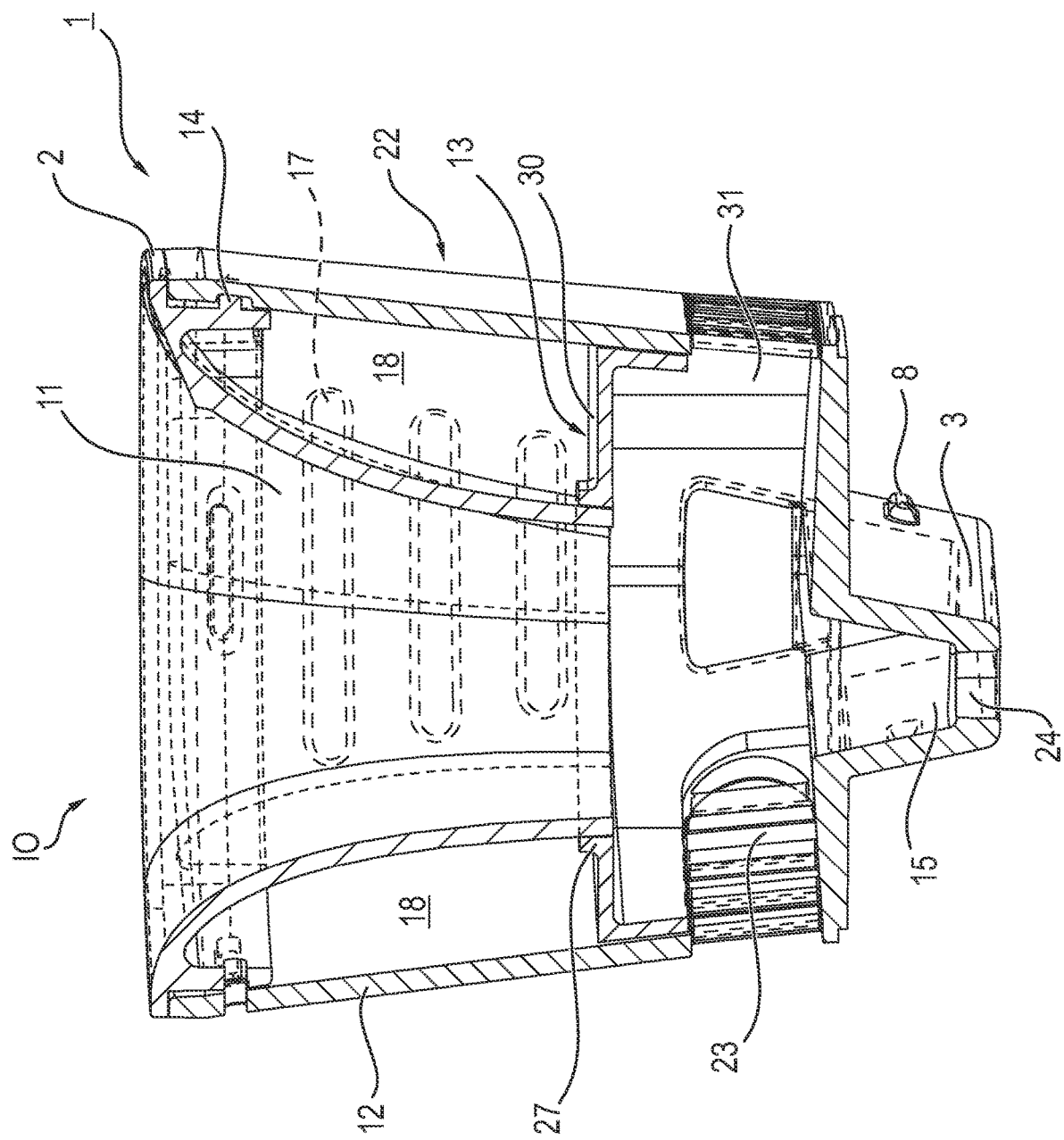
FIG. 7 is a cross-sectional view the first embodiment with the assembled parts wherein a shorter axis (corresponding to a shorter dimension) is in the drawing plane.
Figure 8:
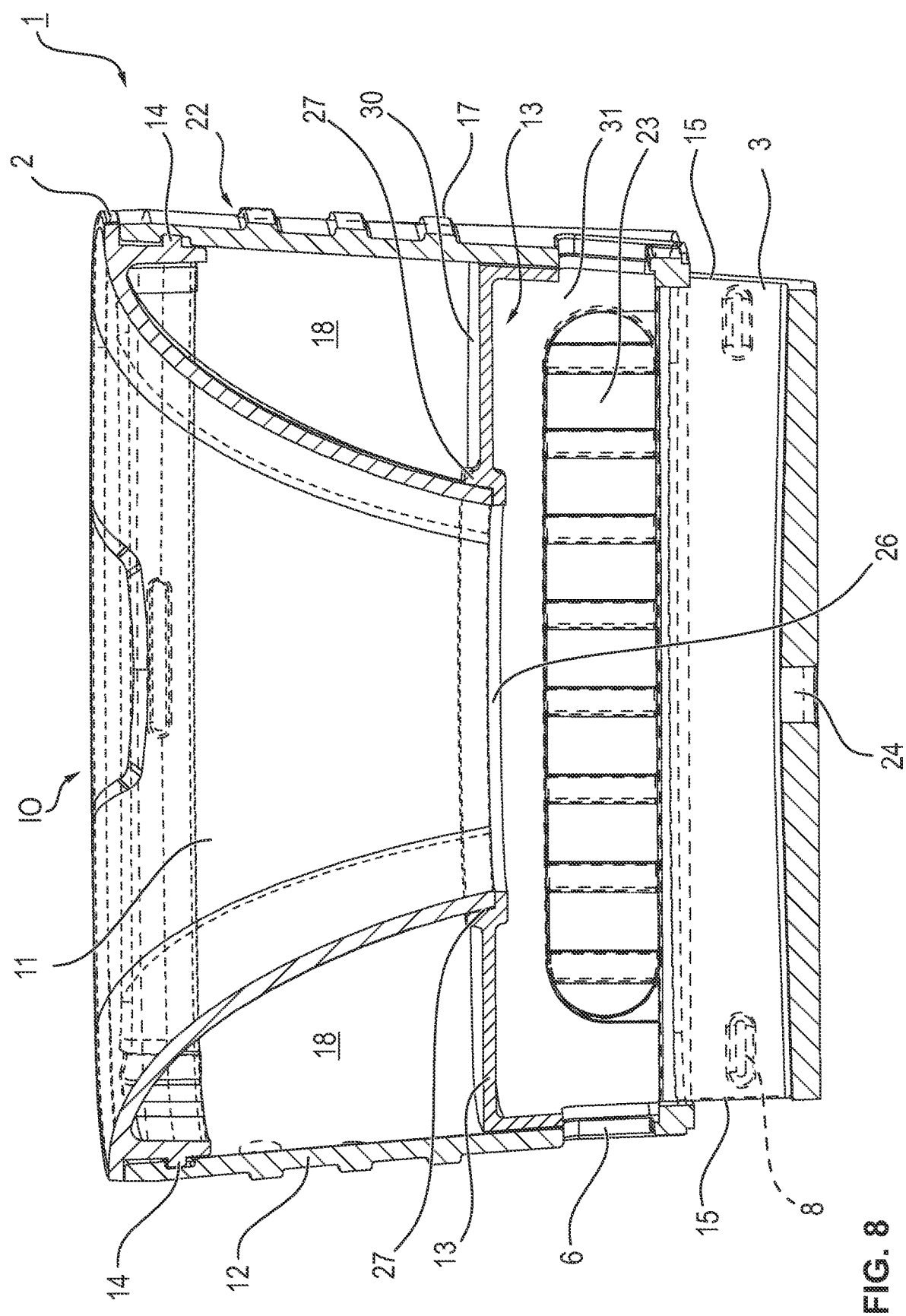
FIG. 8 is a cross-sectional view the first embodiment with the assembled parts wherein the longer axis is in the drawing plane.
Figure 9:
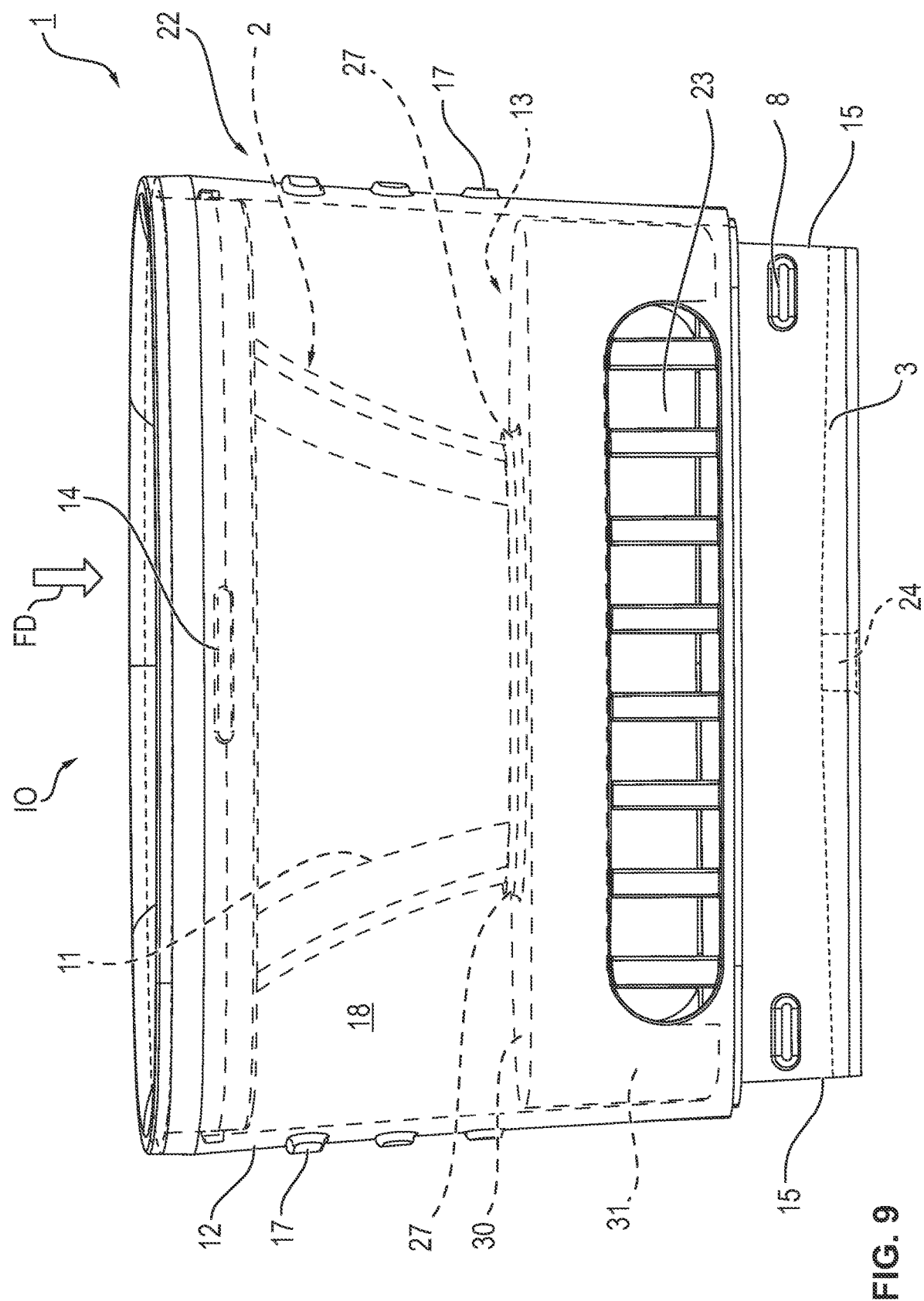
FIG. 9 is a side view the first embodiment.

FIG. 2 and FIG. 3 show the sample collector 1. The sample collector 1 comprises an inflow part 2 with a guiding element 11, an outflow part 13, an optional collector outlet 3, and an optional collector casing 22 with an outer wall 12. The inflow part 2 is rigidly or releasably connected with the outflow part 13. The two parts 2, 13 together form the core sample collector. The core sample collector 2, 13 can be inserted into the collector casing 22 and can be removed from the collector casing 22. The collector casing 22 holds the core sample collector 2, 13, e.g. by means of a click-stop connection. FIG. 2 shows, in a perspective view, the sample collector 1 with the parts 2, 13 not yet being inserted, FIG. 3 in a cross-sectional view the sample collector 1 with the parts 2, 13 being inserted.

Several fastening elements 14 fasten the inserted inflow part 2 at the inner side of the outer wall 12 of the collector casing 22. In one implementation every fastening element is a protrusion which engages a corresponding aperture in the outer wall 12. Several gripping elements 17 make it easier for a person to grasp and hold the collector casing 22.

In one embodiment described below the outflow part 13 between the guiding element 11 and the collector casing 22 implements an abrupt change in the cross section, cf. FIG. 2 and the first embodiment described below.

In one application, the core sample collector 2, 13 is used for taking one sample and is afterwards replaced with a new one. It is also possible to reuse the core sample collector 2, 13 several times, i.e. for several gas samples.

The elliptic inflow part 2 provides an elliptic inflow opening IO through which a gas sample can flow into the device 100, cf. FIG. 16. The inflow part 2 further provides an inflow part transition aperture 32 which is opposite to the inflow opening IO. The guiding element 11 tapers in a direction toward the inflow part transition aperture 32. As can be seen, the inflow part 2 tapers in a parabolic manner, i.e. the reduction of the cross-sectional area decreases towards the inflow part transition aperture 32. Preferably the guiding element 11 has the form of a cone or hopper.

The elliptic outflow part 13 provides an elliptic outflow opening OO through which a gas sample can flow towards the collector outlet 3. The outflow part 13 further provides an outflow part transition aperture 26 which is opposite to the outflow opening OO. The core sample collector 2, 13 of the embodiments therefore provides a kind of nozzle for guiding the gas sample along a flow duct.

The core sample collector 2, 13 forms the housing for a main flow duct 10. A gas sample from a person to be tested is injected through the inflow opening IO and flows through the main flow duct 10 towards the outflow opening OO and through the outflow opening OO into the collector outlet 3. Gas can only "enter" into or "escape" from the core sample collector 2, 13 through the inflow opening IO or through the outflow opening OO.

A gas sample can leave the core sample collector 2, 13 into the collector outlet 3. The gas sample can leave the collector outlet 3 and therefore the sample collector 1 through a central opening 24 into the gas duct 21, cf. FIG. 1b,
through lateral openings 15 on the bottom side of the collector outlet 3 into the environment 7 or
through outflow openings 6 in the collector casing 22 into the environment 7.

Two small openings 6 are formed at the short side of the collector casing 22 and two large openings 6 at the longer side of the collector casing 22. Several stiffeners form slotted apertures 23 in the large openings 6. The gas duct 21 leads into the interior of the base body 9. The guiding element 11 provides the main flow duct 10 and prevents any large amount of gas flowing back towards the inlet opening IO of the inflow part 2. A dead space 18 is formed between the core sample collector 2, 13 and the collector casing 22.

Figure 10:
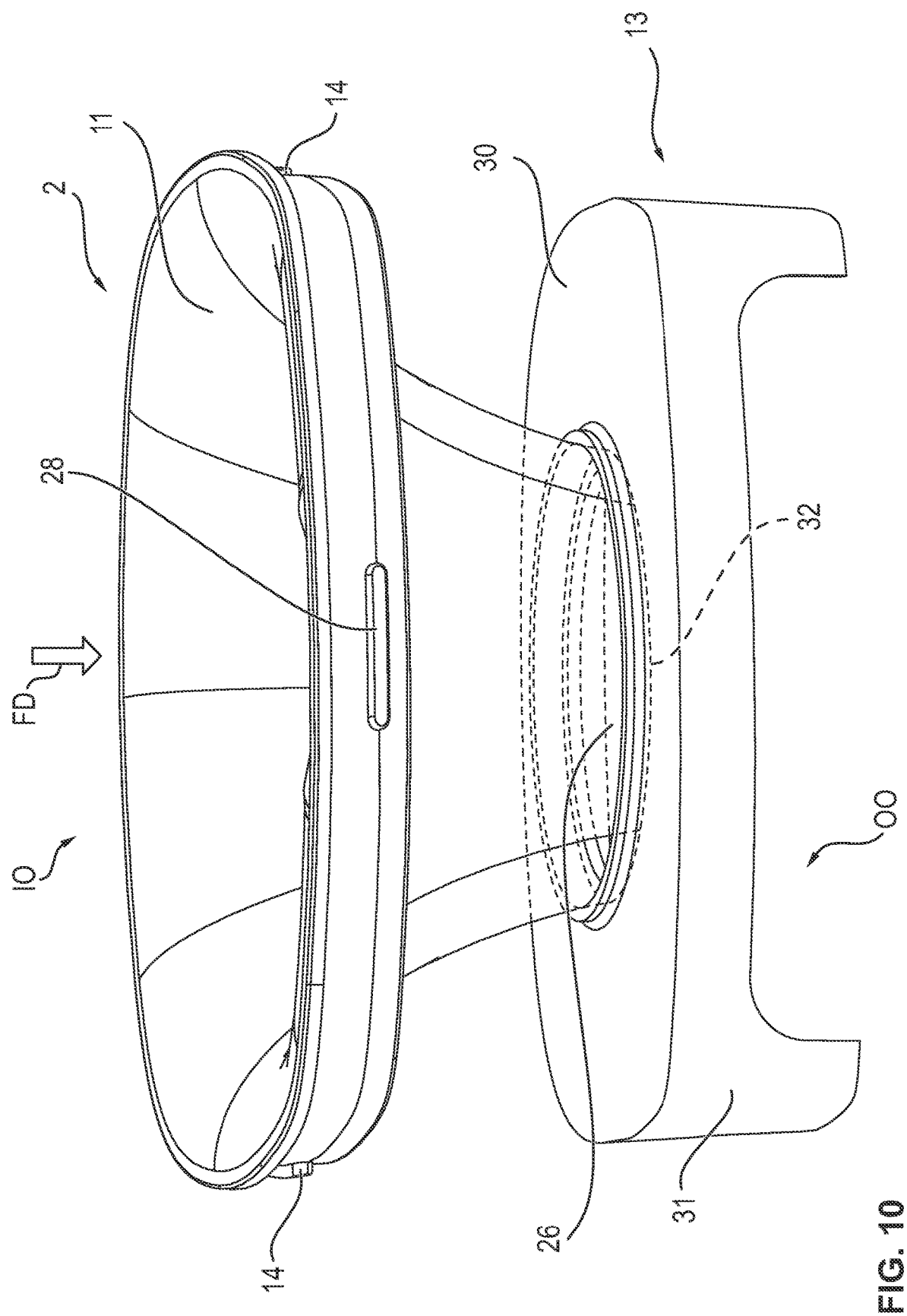
FIG. 10 is a perspective view of the inflow part and the outflow part.
Figure 11:
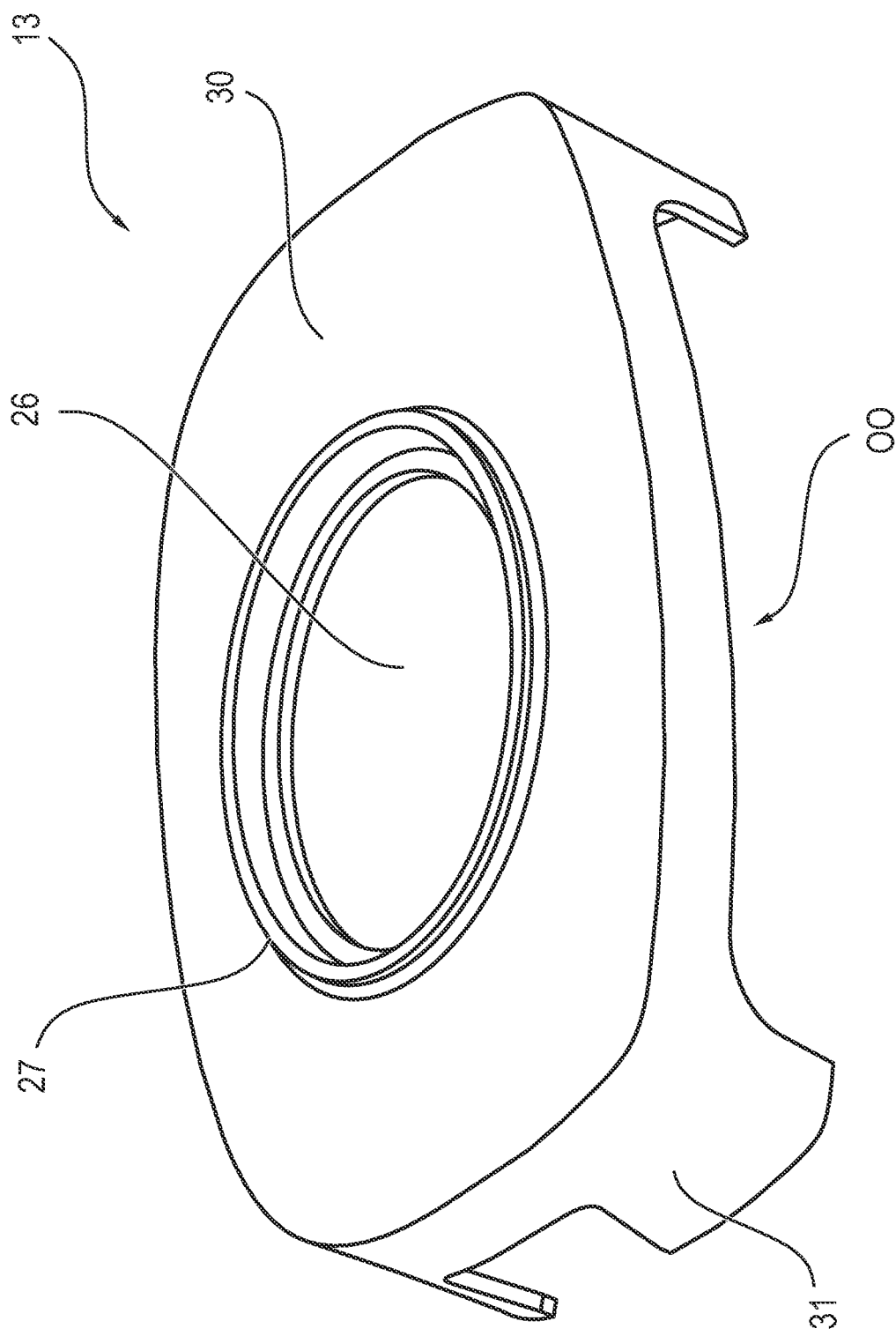
FIG. 11 is a perspective view of the outflow part.
Figure 12:
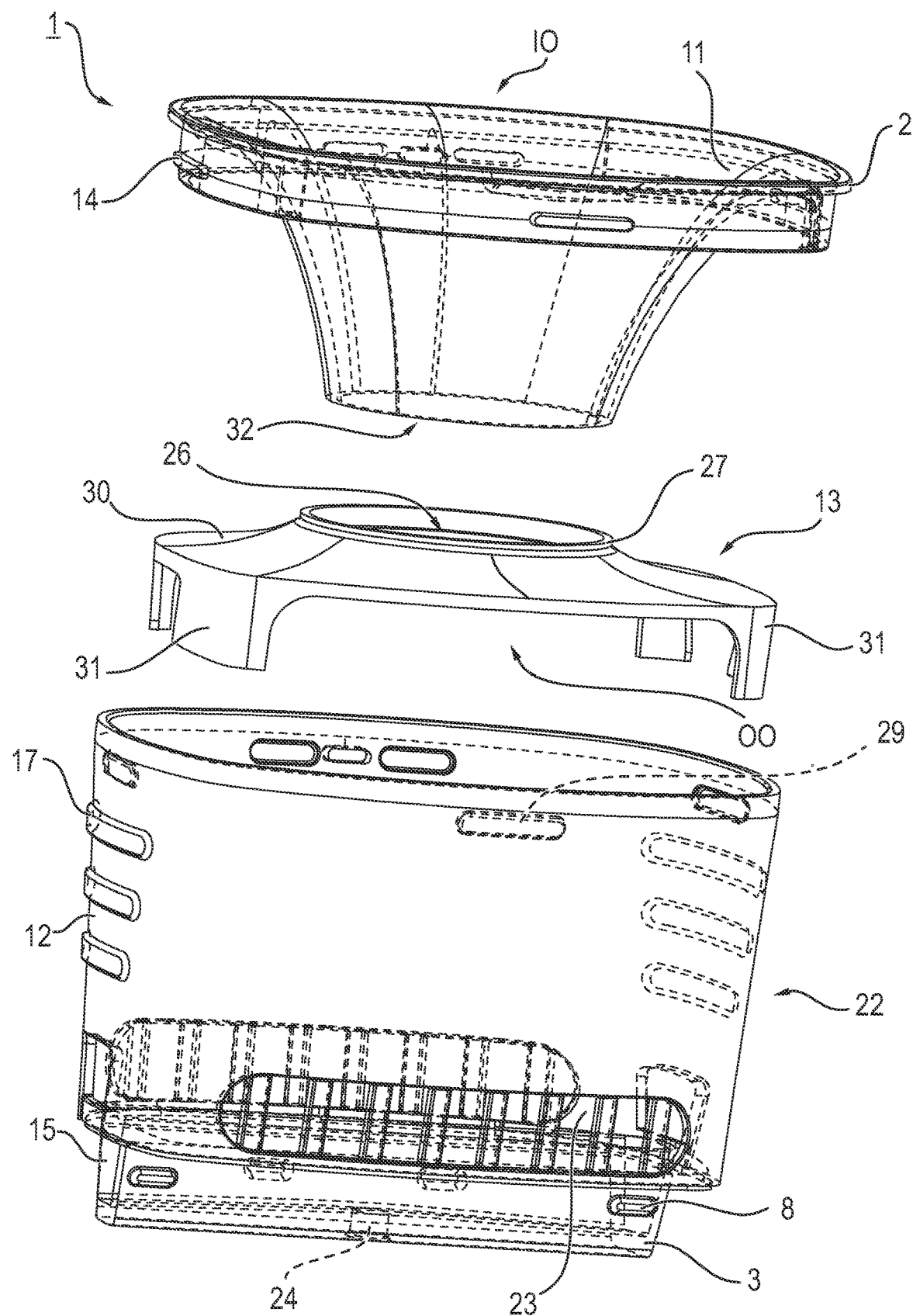
FIG. 12 is an exploded perspective view of a second embodiment of the sample collector with a curved outflow part.
Figure 13:
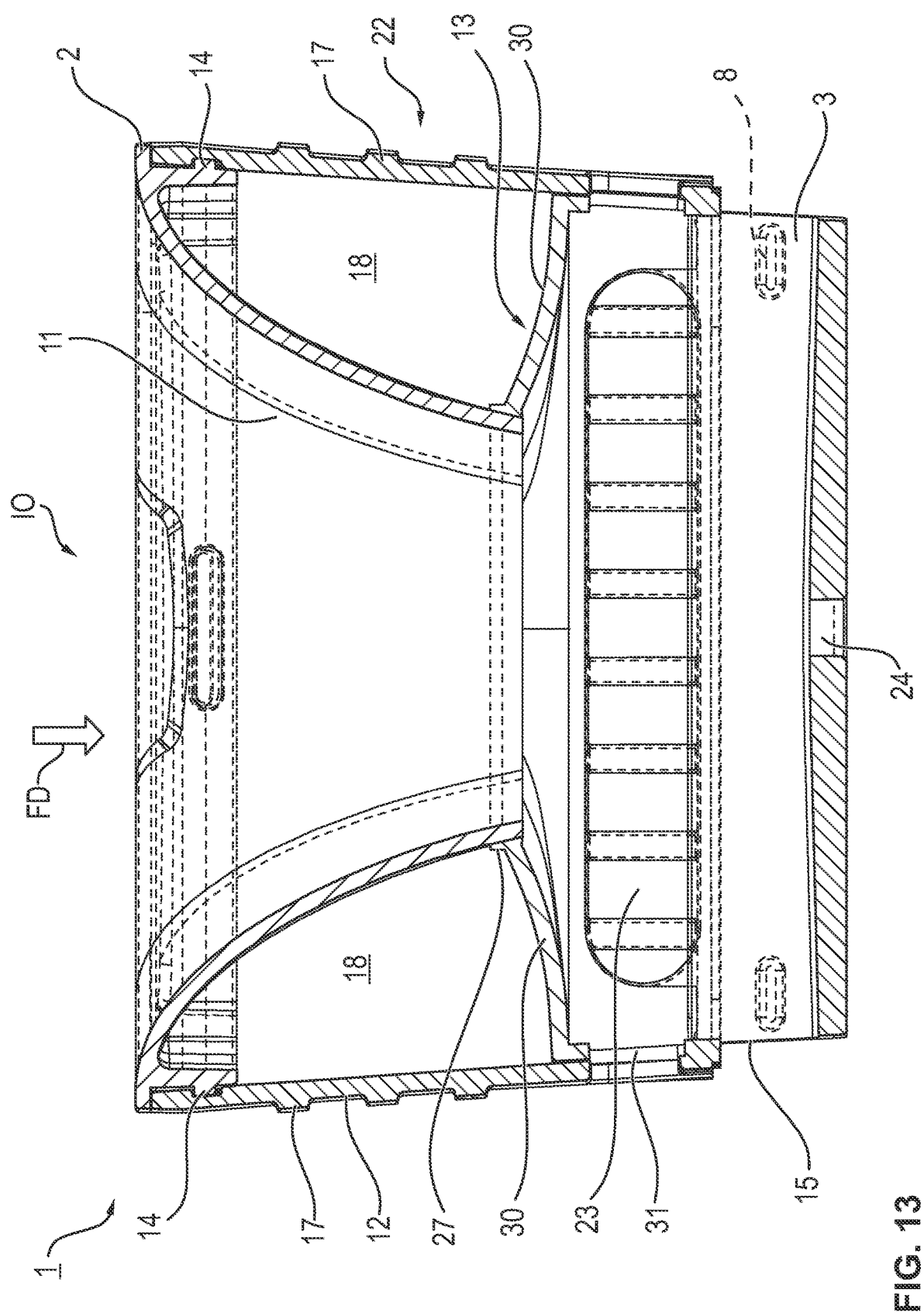
FIG. 13 is a cross-sectional view the second embodiment with the assembled parts wherein the longer axis is in the drawing plane.
Figure 14:
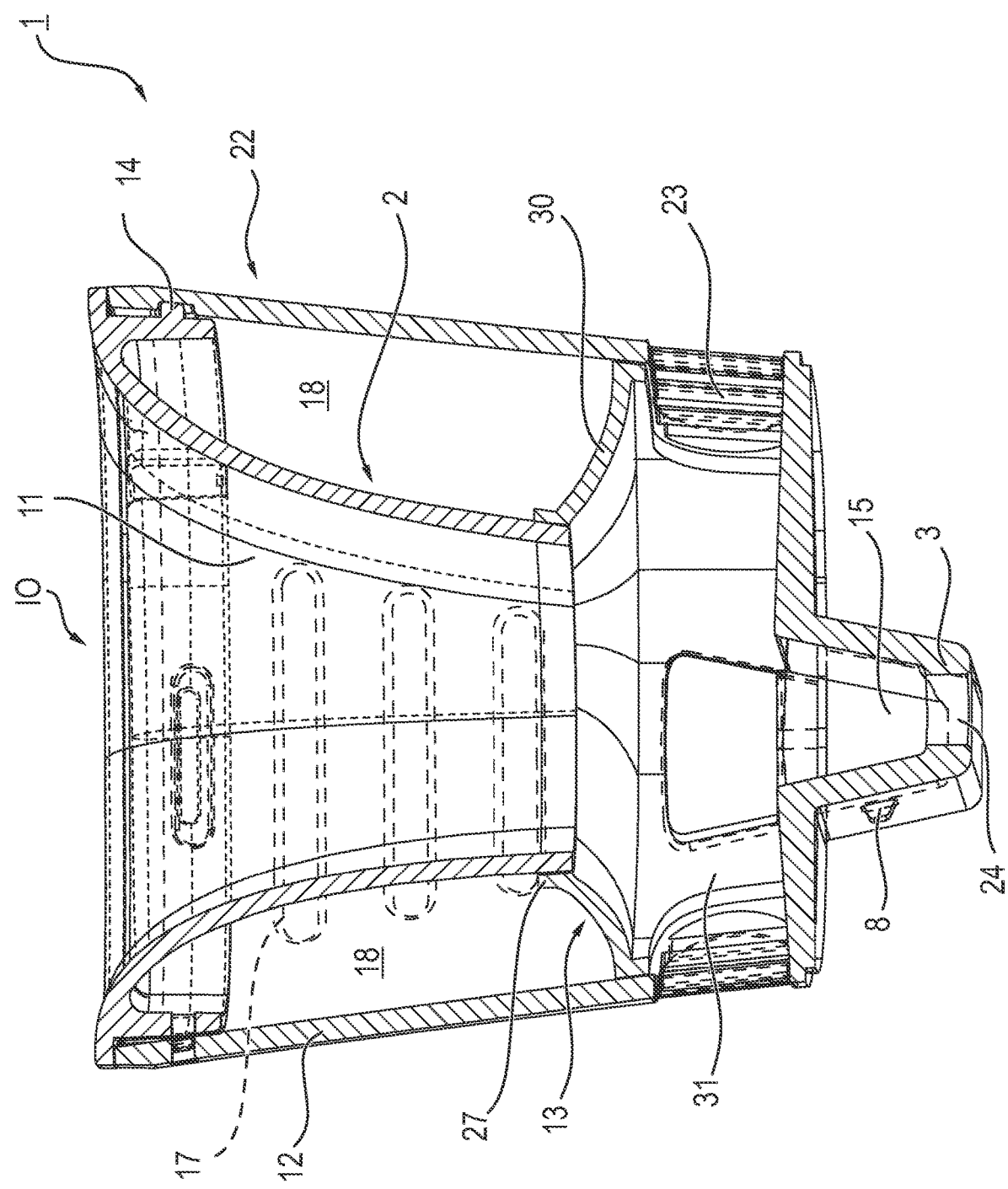
FIG. 14 is a cross-sectional view the second embodiment with the assembled parts wherein the shorter axis is in the drawing plane.
Figure 15:
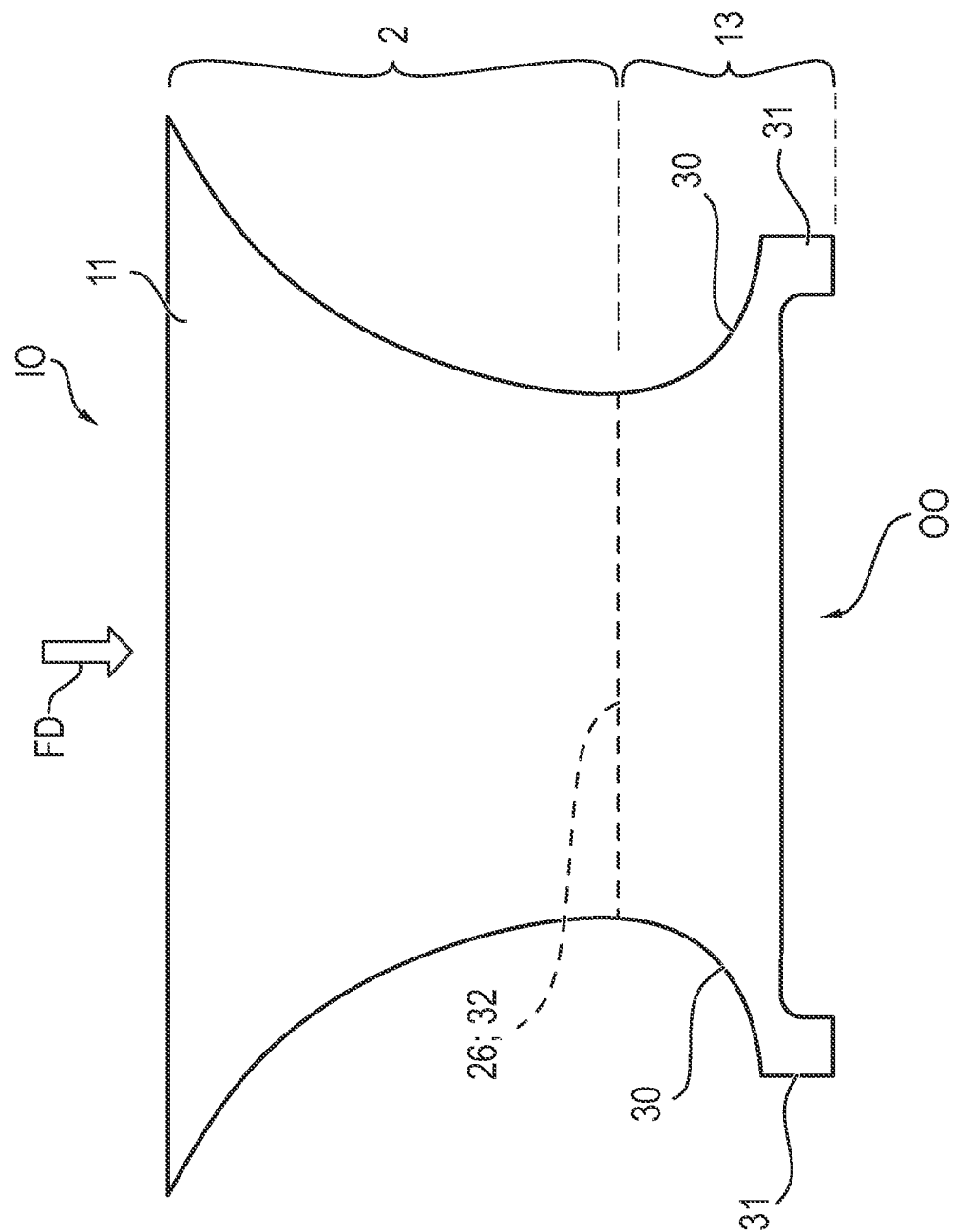
FIG. 15 is a cross-sectional view a third embodiment with an integrally formed core sample collector.

FIG. 4 to FIG. 11 show a first embodiment of the sample collector 1 wherein the outflow part 13 has a flat plane and flat top surface. FIG. 10 shows the core sample collector 2, 13. FIG. 11 shows the outflow part 13 of the first embodiment. FIG. 12 to FIG. 14 show a second embodiment of the sample collector 1 wherein the outflow part 13 has a curvilinear plane and curved top surface. FIG. 15 shows a third embodiment wherein the core sample collector 2, 13 is integrally formed, i.e. made as one piece, and wherein the outflow part 13 also has a curvilinear plane.

The inflow part 2 has the following parts:
the guiding element 11 providing the inflow opening IO,
the protruding fastening elements 14 near the inlet opening IO of the inflow part 2 each forming a bulge engaging a corresponding groove in the inner side of the outer wall 12, and
further protrusions 28 each engaging a corresponding aperture 29 in the outer wall 12.

The outflow part 13 has the following parts:
a flat separator element 30 (first embodiment) or curved separator element 30 (second and third embodiment),
a supporting element 31 engaging the inner side of the outer wall 12 in a laminar manner and providing the outflow opening OO,
the elliptic outflow part transition aperture 26 in the separator element 30 and
a protrusion 27 surrounding the outflow part transition aperture 26.

In the third embodiment according to FIG. 15 the transition apertures 26 and 32 coincide. The inflow part 2 and the outflow part 13 form one unit. In FIG. 10 and FIG. 15 the optional collector casing 22 is not shown.

The optional collector casing 22 is rigidly connected with the collector outlet 3 and has the following parts:
the outer wall 12 with the gripping elements 17,
several apertures 29 each being engaged by a further protrusion 28,
two small openings 6 and two large openings 6 and
optional further openings (not shown) between the inflow opening IO and the separator element 30 providing a fluid connection between the dead space 18 and the environment 7.

The collector outlet 3 comprises the central opening 24 and the lateral openings 15. A rectangular aperture is formed between the collector casing 22 and the collector outlet 3.

The guiding element 11 projects into the elliptic outflow part transition aperture 26. The protrusion 27 surrounds the projecting section of the guiding element 11 in a manner that the connection between the guiding element 11 and the outflow part 13 is a gas-tight one. The connection between the inflow part 2 and the collector casing 22 provided by means of the fastening elements 14 is in one implementation also gas tight. The outer surface of the supporting element 31 contacts the inner surface of the collector casing 22 in a gas-tight manner.

Therefore, no gas which is blown or otherwise injected into the inflow part 2 and flow through the flow duct 10 can enter the dead space 18. In contrast, the collector casing 22 on the outer side and the separator element 30 and the guiding element 11 on the inner side surround the dead space 18 in a gas-tight manner. In particular, the separator element 30 separates the dead space 18 from the outflow openings 6. It is possible that a fluid connection between the dead space 18 and the environment 7 is established.

As can be seen from the exploded view, the inflow part 2, the separator part 13 and the collector casing 22 can be manufactured separately, in particular by using different materials, and can be assembled later.

FIG. 16 shows the inflow opening IO and the inflow part transition aperture 26 wherein the viewing direction is parallel to the flow direction FD. The openings IO, 26 extend in the drawing plane of FIG. 16. The following dimensions are shown:

L1.IO maximal dimension of the inflow opening IO;
L2.IO dimension of the inflow opening IO in a perpendicular direction;
L1.32 maximal dimension of the inflow part transition aperture 32;
L2.32 dimension of the inflow part transition aperture 32 in a perpendicular direction.

Preferred values for these parameters are:
L1.IO: at least 4 cm, preferably no more than 7 cm,
L2.IO: at least 2.5 cm, preferably no more than 5 cm,
L1.32: no more than 4 cm, preferably at least 2 cm,
L2.32: no more than 3 cm, preferably at least 1.5 cm.

Preferably L1.IO is larger than L1.32 and L2.IO is larger than L2.32 such that gas is collected in the inflow part 2. In a further preferred implementation L1.32 is between 35% and 60% of L1.IO. Preferably L2.32 is between 35% and 60% of L2.IO. L1.IO may be above 4 cm, even above 7 cm.

It is also possible that the inflow opening IO has the form of a circle. The diameter of this circle is preferably between 3 cm and 6 cm. The inflow part transition aperture 32 may also be circular, preferably with a diameter between 1.5 cm and 4 cm. Preferably the diameter of the inflow part transition aperture 32 is between 35% and 60% of the diameter of the inflow opening IO.

Preferably the dimension of the outflow opening OO in a plane perpendicular to the flow direction FD is in every direction less than the inflow opening IO, in particular no more than 10% less.

While specific embodiments of the invention have been shown and described in detail to illustrate the application of the principles of the invention, it will be understood that the invention may be embodied otherwise without departing from such principles.

LIST OF REFERENCE SIGNS

1 sample collector, can be removably connected with the base body 9, comprises the inflow part 2, the outflow part 13, the collector casing 22 and the collector outlet 3
2 inflow part, comprises the guiding element 11 and the fastening elements, provides the inflow opening IO
3 collector outlet, rigidly connected with the collector casing 22
4 control unit
5 display unit
6 outflow openings in the collector casing 22
7 area surrounding the testing device 100
8 fastening elements for fastening the sample collector 1 at the base body 9
9 base body, contains the control unit 4 and the power supply 20
10 main flow duct, provided by the guiding element 11 of the inflow part 2, guides from the inflow opening IO to the outflow opening OO
11 guiding element of the inflow part 2, provides the main flow duct 10, has the form of a hopper or cone
12 outer wall of the collector casing 22
13 outflow part, comprises the separator element 30 and the supporting element 31, provides the outflow opening OO
14 fastening elements near the inlet opening of the inflow part 2, can be inserted into a corresponding groove for removably fastening the inflow part 2 at the collector casing 22
15 lateral outlets at the end of the main flow duct 10
16 alcohol sensor
17 gripping elements at the collector casing 22
18 dead space in the inflow part 2, formed around the guiding element 11
20 power supply
21 gas duct, leads from the sample collector 1 to the alcohol sensor 16
22 collector body of the sample collector 1, carries and surrounds the inflow part 2
23 slotted apertures in the openings 6
24 central opening on the bottom side of the collector outlet 3, leads into the gas duct 21
25 gripping elements of the base body 9
26 elliptic outflow part transition aperture, provided by the outflow part 13, surrounded by the protrusion 27
27 protrusion surrounding the outflow part transition aperture 26
28 protrusion near the inflow opening of the inflow part 2
29 protrusion at the collector casing 22
30 flat separator element (first embodiment) or curved separator element (second embodiment) providing an abrupt change, belongs to the outflow part 13
31 supporting element engaging the inner side of the outer wall 12, belongs to the outflow part 13
32 elliptic inflow part transition aperture, provided by the outflow part 13
100 breath alcohol testing device, comprises the sample collector 1 and the base body 9
FD flow direction of gas through the flow duct
IO inflow opening, provided by the inflow part 2
OO outflow opening, provided by the outflow part 13

What is claimed is:
1. A sample collector for receiving a breath gas sample to be investigated, the sample collector comprising:
an inflow part with an inflow opening; and
an outflow part with an outflow opening, the outflow part comprising a separator element and a supporting element;
a collector casing, wherein:
the sample collector provides a flow duct guiding a gas sample from the inflow opening to the outflow opening;
the inflow part and the outflow part together form a housing which gas-tightly surrounds the flow duct;
the collector casing surrounds the housing such that a dead space is provided between the collector casing and the housing;

the separator element bridges a distance between the housing and the collector casing and forms one wall of the dead space;
the supporting element engages an inner side of the collector casing;
the inflow part tapers in a direction towards the outflow opening; and
the outflow part tapers in a direction towards the inflow opening.

2. A sample collector according to claim 1, wherein:
one end of the inflow part is inserted in a direction of the outflow opening to form the housing;
a maximal dimension of the inflow opening is at least 4 cm; and
a maximal dimension of the outflow opening is at least at least 4 cm.

3. A sample collector according to claim 1, wherein:
the inflow part comprises a first inflow part end portion and a second inflow part end portion;
the first inflow part end portion defines the inflow opening;
the inflow part tapers from the first inflow part end portion to the second inflow part end portion in a direction towards the outflow opening;
the second inflow part end portion is in contact with the outflow part;
the second inflow part end portion comprises an inflow part transition aperture and tapers in a direction from the inflow opening towards the inflow part transition aperture; and
the outflow part comprises an outflow part transition aperture and tapers in a direction from the outflow opening towards the outflow part transition aperture.

4. A sample collector according to claim 3, wherein:
a maximal dimension of the inflow part transition aperture is no more than 3 cm; and
a maximal dimension of the outflow part transition aperture is no more than 3 cm.

5. A sample collector according to claim 3, wherein:
the outflow part comprises an outflow part protrusion surrounding the outflow part transition aperture;
an engaging section of the second inflow part end portion engages into the outflow part transition aperture; and
the outflow part protrusion encircles the engaging section of the second inflow part end portion.

6. A sample collector according to claim 3, wherein:
the second inflow part end portion comprises an inflow part protrusion surrounding the inflow part transition aperture;
an engaging section of the outflow part engages into the inflow part transition aperture; and
the inflow part protrusion encircles the engaging section of the outflow part.

7. A sample collector according to claim 1, further comprising a collector outlet with at least one outlet aperture, wherein the collector outlet guides a gas sample, which sample has passed the flow duct, towards the at least one outlet aperture.

8. A sample collector according to claim 1, further comprising a collector outlet with at least one outlet aperture, wherein:
the collector outlet guides a gas sample, which sample has passed the flow duct, towards the at least one outlet aperture; and
the collector casing mechanically connected with the collector outlet.

9. A sample collector according to claim 1, wherein the collector casing comprises a collector casing inner surface defining a collector casing interior space of the collector casing, the outflow part comprising an outflow part outer surface, the outflow part outer surface being in contact with a portion of the collector casing inner surface, at least a portion of the outflow part being arranged in the collector casing interior space, the outflow part further comprising an outflow part space, the outflow part space not being in fluid communication with the dead space.

10. A gas sample testing device comprising:
a sample collector for receiving a breath gas sample to be investigated, the sample collector comprising: an inflow part with an inflow opening; and an outflow part with an outflow opening, the outflow part comprising a separator element and a supporting element; a collector casing, wherein the sample collector provides a flow duct guiding a gas sample from the inflow opening to the outflow opening, the inflow part and the outflow part together form a housing which gas-tightly surrounds the flow duct, wherein the collector casing surrounds the housing such that a dead space is provided between the collector casing and the housing, the separator element bridges a distance between the housing and the collector casing and forms one wall of the dead space, the supporting element engages an inner side of the collector casing, the inflow part tapers in a direction towards the outflow opening, and the outflow part tapers in a direction towards the inflow opening; and
a base body, the base body comprising a gas sensor, wherein:
the sample collector is mechanically connected with the base body;
the outflow opening of the sample collector points towards the base body;
the sample collector is configured to guide a received gas sample towards the base body; and
the gas sensor is configured to detect at least one substance in a received gas sample.

11. A gas sample testing device according to claim 10, wherein:
the sample collector further comprises a collector outlet with at least one first outlet aperture and at least one second outlet aperture;
the collector outlet is configured to guide a gas sample that has passed the flow duct towards the at least one first outlet aperture and the at least one second outlet aperture; and
the collector outlet is configured to distribute the gas sample to the first and second outlet apertures;
the at least one first outlet aperture is configured to lead a gas sample to the gas sensor; and
the at least one second outlet aperture is configured to lead a gas sample into an environment of the gas sample testing device.

12. A gas sample testing device according to claim 10, wherein:
the sample collector is configured to receive a gas breath sample from a person to be tested on alcohol or a further mind-altering substance; and
the gas sensor is configured to detect alcohol or the further mind-altering substance in a received breath sample.

13. A gas sample testing device according to claim 10, wherein:
the inflow part comprises a first inflow part end portion and a second inflow part end portion;

the first inflow part end portion defines the inflow opening;

the inflow part tapers from the first inflow part end portion to the second inflow part end portion in a direction towards the outflow opening;

the second inflow part end portion is in contact with the outflow part;

the second inflow part end portion comprises an inflow part transition aperture and tapers in a direction from the inflow opening towards the inflow part transition aperture; and the outflow part comprises an outflow part transition aperture and tapers in a direction from the outflow opening towards the outflow part transition aperture.

14. A gas sample testing device according to claim 13, wherein:

the outflow part comprises an outflow part protrusion surrounding the outflow part transition aperture;

an engaging section of the second inflow part end portion engages into the outflow part transition aperture; and the outflow part protrusion encircles the engaging section of the second inflow part end portion.

15. A gas sample testing device according to claim 13, wherein:

the second inflow part end portion comprises an inflow part protrusion surrounding the inflow part transition aperture;

an engaging section of the outflow part engages into the inflow part transition aperture; and the inflow part protrusion encircles the engaging section of the outflow part.

16. A gas sample testing device according to claim 10, wherein:

the sample collector comprises a collector outlet with at least one outlet aperture;

the collector outlet guides a gas sample, which sample has passed the flow duct, towards the at least one outlet aperture.

17. A gas sample testing device according to claim 10, wherein:

the sample collector comprises a collector outlet with at least one outlet aperture;

the collector outlet guides a gas sample, which sample has passed the flow duct, towards the at least one outlet aperture; and the collector casing is mechanically connected with the collector outlet.

18. A gas sample testing device according to claim 10, wherein the collector casing comprises a collector casing inner surface defining a collector casing interior space of the collector casing, the outflow part comprising an outflow part outer surface, the outflow part outer surface being in contact with a portion of the collector casing inner surface, at least a portion of the outflow part being arranged in the collector casing interior space, the outflow part further comprising an outflow part space, the outflow part space not being in fluid communication with the dead space.

* * * * *